Oct. 1, 1968 A. M. SHAMMARELLO Plant Pat. 2,837
SEMI-DOUBLE WHITE AZALEA PLANT
Filed Dec. 16, 1966
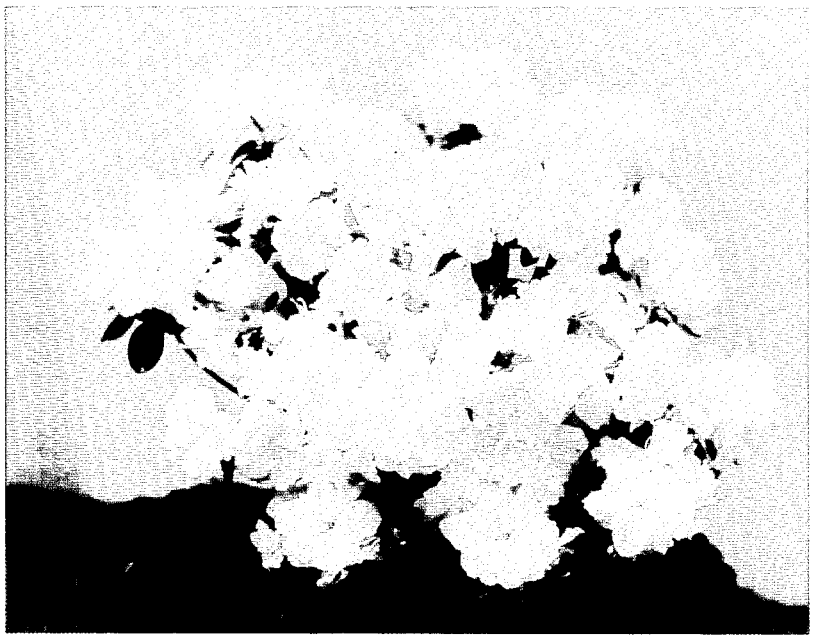

United States Patent Office

Plant Pat. 2,837
Patented Oct. 1, 1968

2,837

SEMI-DOUBLE WHITE AZALEA PLANT

Anthony M. Shammarello, 4590 Monticello Blvd., Cleveland, Ohio 44121

Filed Dec. 16, 1966, Ser. No. 602,432
1 Claim. (Cl. Plt.—55)

The present invention relates to a new and distinct variety of azalea plant of the Kurume type, and is the result of a definite breeding program.

The principal object of this breeding program was to produce a new hardy semi-double white flower azalea. Such a plant is not known to me in northern Ohio.

The foregoing objective has been obtained in my new variety by a hardy plant with semi-double white flower and retention of foliage throughout the winter.

*Seed parent.*—Azalea "Desiree"—Plant Patent No. 2,068, granted July 4, 1961, to Anthony M. Shammarello, the applicant herein.

*Pollen parent.*—Azalea "Rosebud" (Gable).

Azalea "Rosebud" is not patented.

My new variety has been found to retain its distinctive characteristics through successive asexual reproduction by means of cutting in the vicinity of South Euclid, Ohio.

The hardness of the plant and flower buds of my new variety is indicated by the fact they were not adversely affected by a temeprature of 15 degrees below zero the winter of 1965–1966 in the vicinity of South Euclid, Ohio.

The flowers of my new variety are about two and a half inches wide, composed of three rows of florets.

The accompanying drawing, forming a part hereof, shows a typical plant of my new variety of azalea, the color of the latter being as nearly true as it is reasonably possible to make the same in a color illustration of this character.

The following is a detailed description of my new variety of azalea plant, color reference being to Munsell Neutral Value Scale published by the Munsell Color Company:

Type: Hardy-evergreen.
Parentage: Seedling.
Seed parent: Azalea "Desiree" Plant Patent No. 2,068.
Pollen parent: Azalea "Rosebud."

*Plant*

Form of plant: Bushy-compact.
Growth habit: Medium; from a cutting, attaining a height of about two feet and a width of about three feet in ten years.
Blooming season: About May 25th. (Color reference to Nickerson Color Fan.)
Young shoots: Stems color 2.5GY 6/8 strong yellow green.
Mature shoots: Stems color 10YR 4/4 moderate yellowish-brown.
Foliage:
*Color of young leaves (obverse).*—7.5GY 4/4 moderate olive green.
*Color of mature leaves (obverse).*—5GY 4/3 moderate olive green.
*Color of leaves (reverse).*—7.5GY 5/7 moderate yellow green.
*Arrangement of leaves.*—In a spiral.
*Form of leaves.*—Elliptical.
*Size of leaves.*—1½" to 1¾" long, ¾" to ⅞" wide.
*Leaf texture.*—Firm.
*Pubescence of leaves.*—Short brown hairs covering all of underside area.

*Flower*

Type: Semi-double, three rows of petals.
Borne: Usually three in a cluster.
Quantity: Abundant.
Form: Fifteen petals.
Size: Petals spread 2¼" to 2½" wide.
Color: White N9.5, 90% R.
Blotch: Speckled green.
Petal texture: Firm, with substance.
Fragrance: None.
Stamens: Color—white. One to two stamens individually formed, five to six stamens attached to floret. Stamens ¾ to one inch long.
Pistil: Color—white, 1" to 1¼" long.
Flower bud hardiness: Fifteen degrees below zero.

I claim:

1. A new and distinct variety of azalea plant of the hardly evergreen type, substantially as herein shown and described, characterized particularly as to novelty by its semi-double white flower, by the hardiness of plant and flower buds at low temperature, and by its bushy-compact shape.

No references cited.

ROBERT E. BAGWILL, *Primary Examiner.*